(12) United States Patent
Ainsworth et al.

(10) Patent No.: US 7,819,833 B2
(45) Date of Patent: Oct. 26, 2010

(54) METHODS TO PERFORM MINIMALLY INVASIVE SURGERIES

(75) Inventors: Robert D. Ainsworth, Scotts Valley, CA (US); Hongzhi Bai, Sunnyvale, CA (US); Greg Hyde, Menlo Park, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 386 days.

(21) Appl. No.: 11/746,433

(22) Filed: May 9, 2007

(65) Prior Publication Data

US 2007/0208298 A1    Sep. 6, 2007

Related U.S. Application Data

(62) Division of application No. 10/184,868, filed on Jun. 28, 2002, now Pat. No. 7,241,257.

(51) Int. Cl.
*A61M 37/00* (2006.01)
(52) U.S. Cl. ................................ 604/4.01; 604/523
(58) Field of Classification Search ............ 604/4.01, 604/6.16, 523; 623/1.1, 1.23, 1.24, 2.11, 623/3.1, 904
See application file for complete search history.

(56) References Cited

U.S. PATENT DOCUMENTS

| | | | |
|---|---|---|---|
| 5,112,349 A | 5/1992 | Summers et al. |
| 5,411,552 A | 5/1995 | Andersen et al. |
| 5,507,795 A | 4/1996 | Chiang et al. |
| 5,632,754 A | 5/1997 | Farley et al. |
| 5,702,368 A | 12/1997 | Stevens et al. |
| 5,713,849 A | 2/1998 | Bosma et al. |
| 5,758,666 A | 6/1998 | Larson, Jr. et al. |
| 5,840,081 A | 11/1998 | Andersen et al. |
| 5,911,685 A | 6/1999 | Siess et al. |
| 5,947,892 A | 9/1999 | Benkowski et al. |
| 5,947,995 A | 9/1999 | Samuels |
| 6,010,531 A | 1/2000 | Donlon et al. |
| 6,022,336 A | 2/2000 | Zadno-Azizi et al. |
| 6,044,845 A | 4/2000 | Lewis |

(Continued)

OTHER PUBLICATIONS

Abbott Cardiovascular Systems, Final office action dated Dec. 9, 2009 for U.S. Appl. No. 11/746,424.

(Continued)

*Primary Examiner*—Tatyana Zalukaeva
*Assistant Examiner*—Benedict L. Hanrahan
(74) *Attorney, Agent, or Firm*—Jonathan Feuchtwang; Blakely, Sokoloff, Taylor & Zafman LLP (57) ABSTRACT

In one embodiment, there is disclosed a device adapted to be used for percutaneous minimally invasive heart surgery including a catheter having a proximal end and a distal end adapted to be fed through a blood vessel, a pump associated with the distal end of the catheter, and a tool associated with the distal end of the catheter. The tool is adapted to be used for percutaneous minimally invasive heart surgery. Examples of the tools include a tool for excising natural tissue, a tool for excising a natural valve, and anthretomy device, a prosthetic valve delivery system, a balloon catheter, a knife, a stapler, and a screwdriver. The pump is used for maintaining blood flow around the site of the heart surgery while the surgery is taking place without the use of cardiopulmonary bypass.

13 Claims, 8 Drawing Sheets

U.S. PATENT DOCUMENTS

| | | |
|---|---|---|
| 6,136,025 A | 10/2000 | Barbut et al. |
| 6,168,614 B1 | 1/2001 | Andersen et al. |
| 6,176,848 B1 | 1/2001 | Rau et al. |
| 6,193,704 B1 | 2/2001 | Winters |
| 6,260,552 B1 | 7/2001 | Mortier et al. |
| 6,283,127 B1 | 9/2001 | Sterman et al. |
| 6,312,447 B1 | 11/2001 | Grimes |
| 6,425,916 B1 | 7/2002 | Garrison et al. |
| 6,443,966 B1 * | 9/2002 | Shiu ............................ 606/159 |
| 2001/0004675 A1 | 6/2001 | Woodward et al. |
| 2001/0018611 A1 | 8/2001 | Solem et al. |
| 2001/0027287 A1 | 10/2001 | Shmulewitz et al. |
| 2001/0031907 A1 | 10/2001 | Downey et al. |
| 2002/0007190 A1 | 1/2002 | Wulfman et al. |
| 2002/0026944 A1 | 3/2002 | Aboul-Hosn et al. |
| 2002/0058995 A1 * | 5/2002 | Stevens ...................... 623/2.11 |
| 2002/0198550 A1 | 12/2002 | Nash et al. |
| 2005/0049696 A1 * | 3/2005 | Siess et al. ................. 623/2.11 |

OTHER PUBLICATIONS

Abbott Cardiovascular Systems, Non final office action dated Jun. 23, 2010 for U.S. Appl. No. 11/746,424.

Abbott Cardiovascular Systems, Non final office action dated Jun. 22, 2010 for U.S. Appl. No. 11/614,963.

* cited by examiner

METHODS TO PERFORM MINIMALLY INVASIVE SURGERIES

CROSS-REFERENCE TO RELATED APPLICATION

This application is a divisional of U.S. patent application Ser. No. 10/184,868, filed Jun. 28, 2002 now U.S.Pat.7,241,257.

BACKGROUND

1. Field

This invention relates to minimally invasive surgeries that may be performed percutaneously.

2. Description of Related Art

Generally, catheters, replacement valves, splints, and other devices for performing procedures and surgeries within a blood vessel are known in the art. U.S. Pat. No. 5,947,995 discloses a catheter. U.S. Pat. No. 6,168,614 discloses a valve prosthesis. U.S. Pat. No. 6,260,552 discloses a splint. U.S. Patent Application No. 2001/0018611, published on Aug. 30, 2001, discloses a device. U.S. Pat. No. 6,283,127 discloses devices. U.S. Pat. No. 6,312,447 discloses devices.

Generally, blood pumps are known in the art. U.S. Pat. No. 5,758,666 discloses a pump. U.S. Pat. No. 5,947,892 discloses a blood pump. U.S. Pat. No. 6,136,025 discloses methods for using blood pumps. U.S. Pat. No. 6,176,848 discloses a blood pump. U.S. Patent Application No. 2001/0004675 published on Jun. 21, 2001, discloses a ventricular assist device. U.S. Patent Application No. 2001/0027287, published on Oct. 4, 2001, discloses an apparatus and method of using the apparatus. U.S. Patent Application No. 2001/0031907, published on Oct. 18, 2001, discloses an apparatus for use in human patients. U.S. Patent Application No. 2002/0026944, published on Mar. 7, 2002, discloses a pump.

SUMMARY

In one embodiment, there is disclosed a device adapted to be used for percutaneous minimally invasive heart surgery including a catheter having a proximal end and a distal end adapted to be fed through a blood vessel, a pump associated with the distal end of the catheter, and a tool associated with the distal end of the catheter. The tool is adapted to be used for percutaneous minimally invasive heart surgery. Examples of the tools include a tool for excising natural tissue, a tool for excising a natural valve, an anthretomy device, a prosthetic valve delivery system, a balloon catheter, a stent delivery catheter, a knife, a stapler, a suturing system with sutures, and a screwdriver. The pump is used in one respect for maintaining blood flow around the site of the heart surgery while the surgery is taking place without the use of cardiopulmonary bypass.

In another embodiment, there is disclosed a kit adapted to be used for percutaneous minimally invasive heart surgery including a first catheter adapted to be fed through a blood vessel, wherein the first catheter includes a proximal end and a distal end, a pump associated with the distal end of the first catheter; and a second catheter adapted to be fed through a blood vessel, wherein the second catheter includes a proximal end and a distal end, and a tool associated with the distal end of the second catheter.

In a further embodiment, there is disclosed a method of performing a percutaneous minimally invasive heart surgery including feeding a catheter having a pump associated with a distal end of the catheter into a blood vessel of a patient, placing an inlet of the pump into the patient's left ventricle, placing an outlet of the pump in the patient's aorta, and performing a percutaneous procedure, and pumping blood through the pump around or through the percutaneous procedure. According to a method such as this, a percutaneous procedure can be conducted while maintaining blood flow through the heart and the body without the use of cardiopulmonary bypass.

The features of the described embodiments are specifically set forth in the appended claims. However, the embodiments are best understood by referring to the following description and accompanying drawings, in which similar parts are identified by like reference numerals.

DETAILED DESCRIPTION

Figure 1:
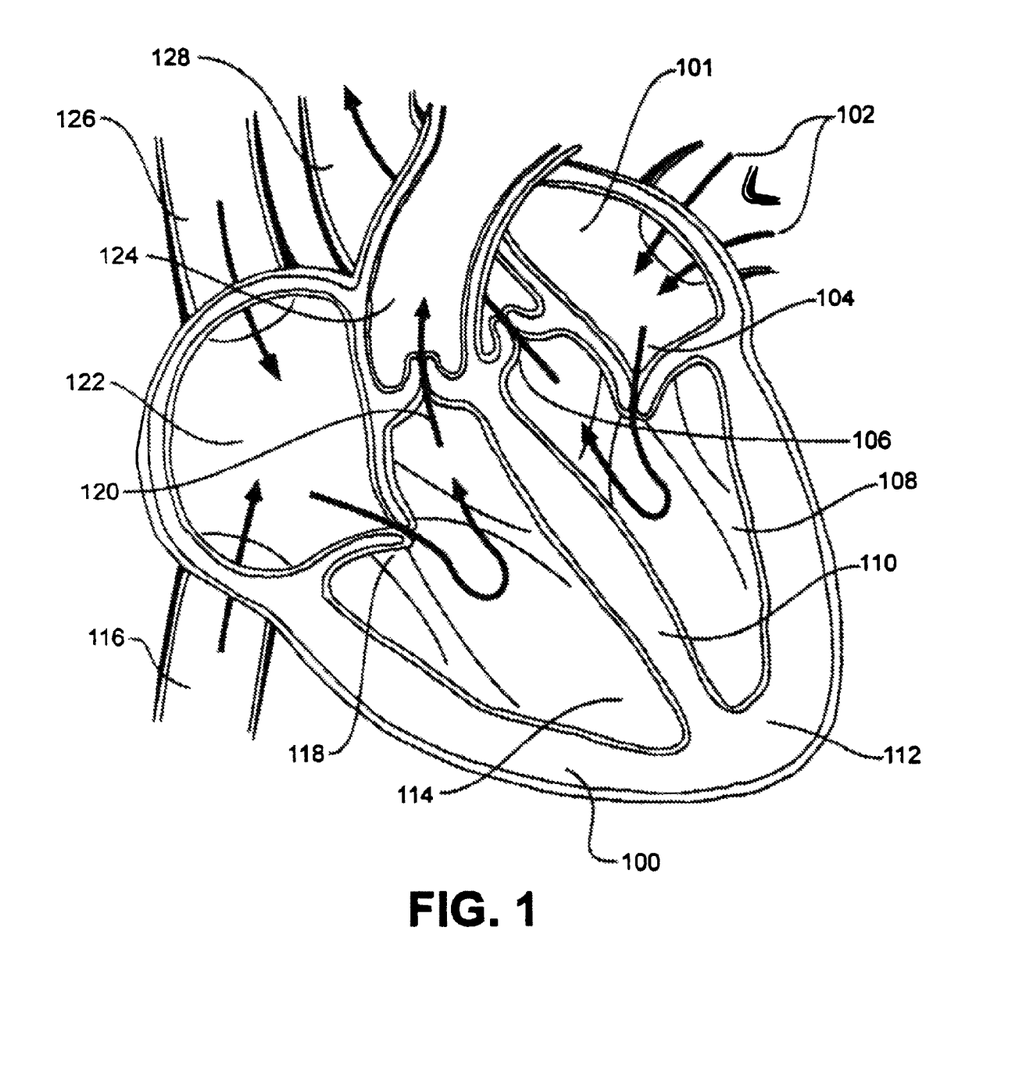
FIG. 1 schematically illustrates a cross-section of the heart showing blood flow throughout the heart.

Referring first to FIG. 1, a simplistic cross-sectional view of a heart is shown to illustrate blood flow throughout the heart.

Deoxygenated blood returning from the body comes into heart 100 from either superior vena cava 126 or inferior vena cava 116 and collects in right atrium 122. Right atrium 122 contracts to pump the blood through tricuspid valve 118 where it flows into right ventricle 114. Right ventricle 114 contracts to send the blood through pulmonary valve 120 into pulmonary artery 124 where it goes into the lungs (not shown). The oxygenated blood returning from the lungs flows through pulmonary veins 102 where it flows into left atrium 101. Left atrium 101 contracts sending the blood through bicuspid or mitral valve 104 and into left ventricle 108. When left ventricle 108 contracts, the blood is sent through aortic valve 106 and into aorta 128. Left ventricle 108 and right ventricle 114 are separated by ventricular septum 110.

If there is a problem with aortic valve 106, when left ventricle 108 expands to take in blood through mitral valve 104 from left atrium 101, left ventricle 108 may also suck blood back into the left ventricle 108 from the aorta 128 through the aortic valve 106. This back flow of blood from aorta 128 into left ventricle 108 can occur if the aortic valve 106 is not properly functioning. In order to repair a nonfunctioning aortic valve 106, a patient's heart is normally arrested and the patient is placed on cardiopulmonary bypass so that a surgery on the aortic valve 106 can be performed. It is difficult to perform a percutaneous aortic valve 106 repair or replacement while the heart is beating, since blood needs to flow through the heart 100 by flowing into pulmonary veins 102 into left atrium 101, through mitral valve 104 into left ventricle 108 across aortic valve 106 and into aorta 128 to be fed to the rest of the body. If there are a number of tools (not shown) that are blocking the aorta 128 that are being used to operate on aortic valve 106, then this blood flow cannot occur normally. In order to perform a surgery on aortic valve 106 without cardiopulmonary bypass, normal blood flow needs to occur through heart 100 and the rest of the body.

Similar problems of heart surgeries or procedures are encountered when working on mitral valve 104, tricuspid valve 118, pulmonary valve 120, and ventricular septum 110. In order to conduct a successful procedure on an area of heart 100, it is necessary to place an inlet of a pump upstream of the area and an outlet of a pump downstream of the area that is going to be worked on, when the area that will be worked on will be blocked by the tools that are used to perform the procedure.

Figure 2:
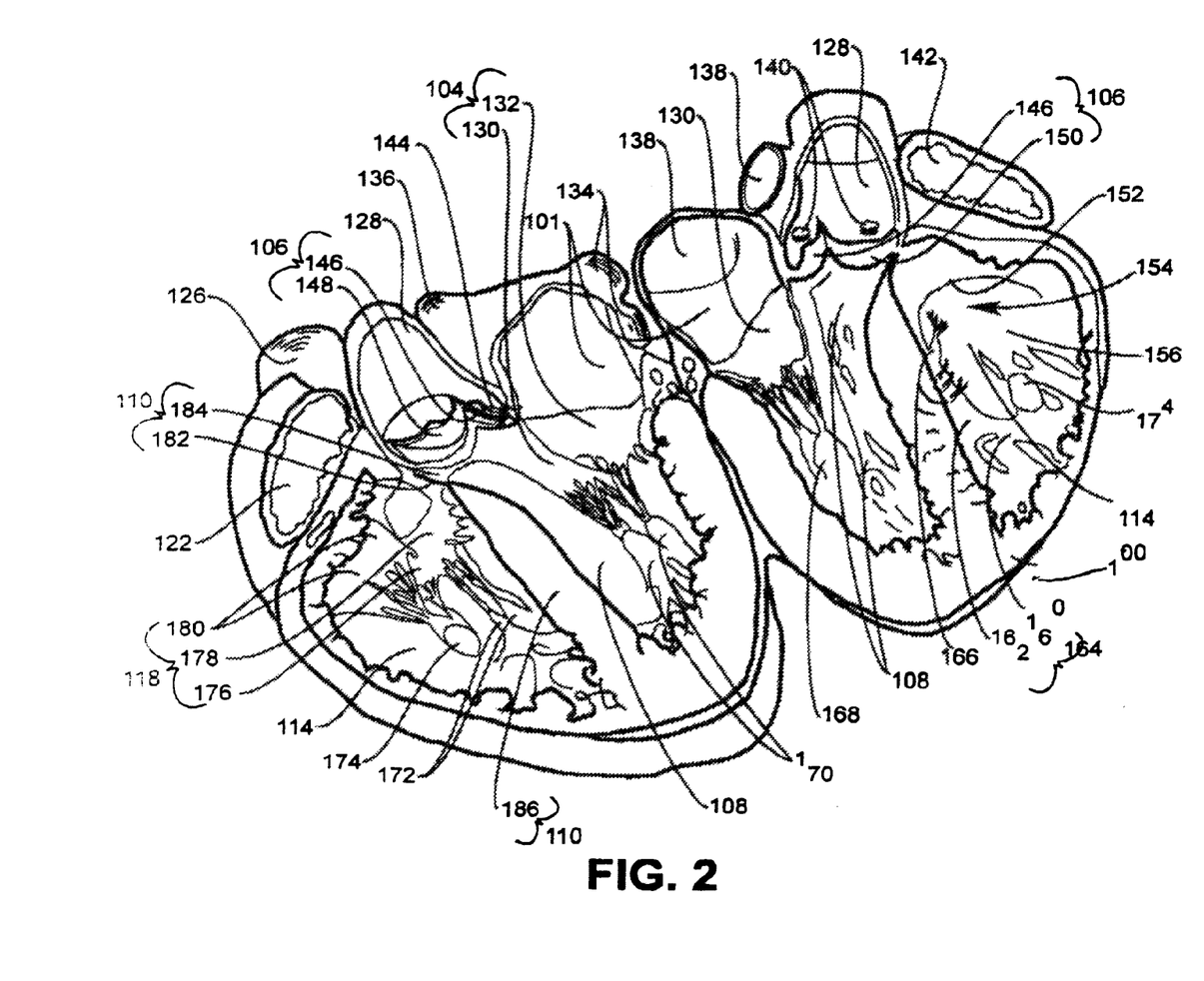
FIG. 2 schematically illustrates a vertical cross-section of the heart.

Referring to FIG. 2, a more detailed vertical cross-section of heart 100 is shown. Blood first collects in right atrium 122 from superior vena cava 126 or other veins. Right atrium 122 also includes right auricle 142. When right atrium 122 contracts, blood is sent through tricuspid valve 118 and into right ventricle 114. Tricuspid valve 118 is made up of three cusps: posterior cusp 176, septal cusp 178, and anterior cusp 180 (shown retracted). Right ventricle 114 has a number of muscles that contract to send blood out of right ventricle 114. Some of the muscles in right ventricle 114 include right anterior papillary muscle 174 (shown cut), and right posterior papillary muscle 172. Other parts of the anatomy of right ventricle 114 includes conus arteriosis 156, supra ventricular crest 152, and moderator band 160 and septal band 162 of septal marginal trabacula 164. The blood outflow to the pulmonary trunk is marked by arrow 154. Pulmonary trunk is shown as 138. The blood returning from the lungs returns by left pulmonary veins 134 and right pulmonary veins 136 where it collects in left atrium 101. Left atrium 101 also includes left auricle 138. When left atrium 101 contracts, blood is sent through mitral valve 104 which is made up of posterior cusp 132 and anterior cusp 130. Blood flows through mitral valve 104 and into left ventricle 108. Muscles in the left ventricle include left posterior papillary muscle 170, left anterior papillary muscle 168. Septum 110 separates left ventricle 108 from right ventricle 114. Septum 110 includes the muscular part of intraventricular septum 186, interventricular part of the membranous septum 182, and the atrial ventricular part of membranous septum 184. When left ventrical 108 contracts, blood is sent through aortic valve 106 which includes left semi-lunar cusp 146, posterior semi-lunar (non-coronary) cusp 148, and right semi-lunar cusp 150. Most of the blood flows through aortic valve 106 and into ascending aorta 128, although some of the blood is diverted into the openings of coronary arteries 140.

Figure 3:
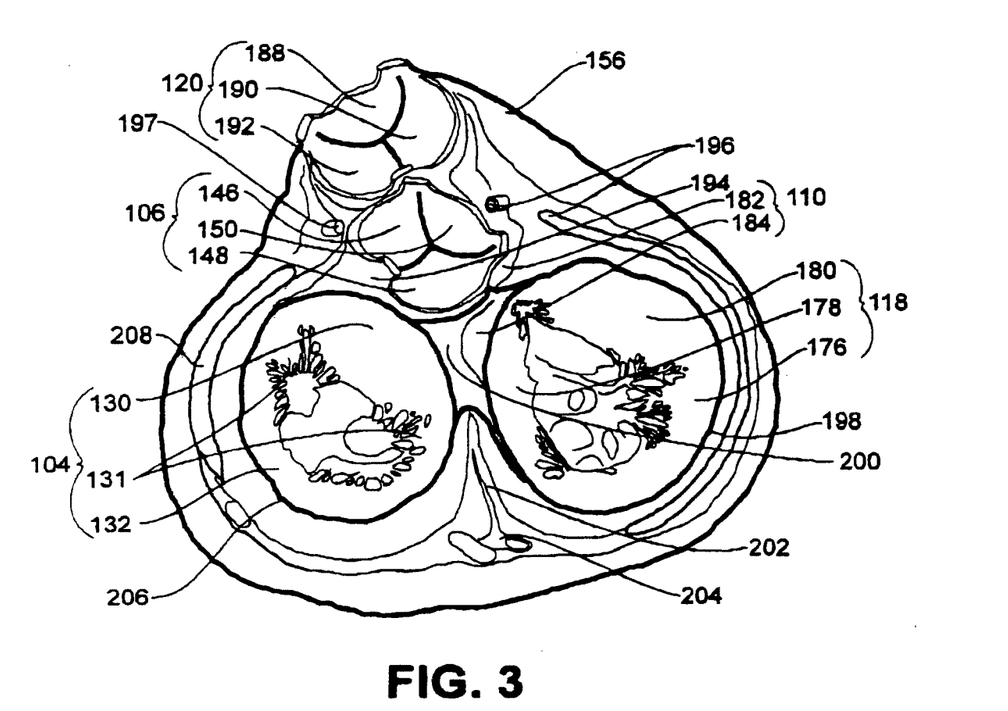
FIG. 3 schematically illustrates a horizontal cross-section of the heart in diastole showing valve operation.

Referring now to FIG. 3, is a horizontal cross-section of the heart showing the heart in diastole viewed from the base with the atria removed. Pulmonary valve 120 is shown in a closed position. Pulmonary valve 120 includes anterior semi-lunar cusp 198, right semi-lunar cusp 190, and left semi-lunar cusp 192. Aortic valve 106 is also shown in a closed position. Aortic valve 106 includes right (coronary) semi-lunar cusp 150, left (coronary) semi-lunar cusp 146, and posterior (non-coronary) semi-lunar cusp 148. The circumflex branch of the left coronary artery is labeled as reference number 208. Mitral valve 104 (between left atrium 101 and left ventricle 108) is shown in an open position. Mitral valve 104 includes anterior cusp 130, posterior cusp 132, and commissural cusps 131. There is also left fibrous ring 206 of mitral valve 104.

At the base of FIG. 3 (as viewed) is the posterior intraventricular branch of right coronary artery 204 and the atrial ventricular nodal branch of right coronary artery 202. In the middle of the heart is right fibrous trigone 200. Tricuspid valve 118 between the right atrium 122 and the right ventricle 114 is shown in an open position and includes anterior cusp 180, septal cusp 178, and posterior cusp 176. Surrounding tricuspid valve 118 is a right fibrous ring of tricuspid valve 198. Membranous septum 110 includes intraventricular part 182 (shown by a broken line) and atrial-ventricular part 184. Right coronary artery is shown as 196, and left coronary artery is shown as 197. Left fibrous trigone is shown as 194, and conus arteriosis is shown as 156.

Figure 4:
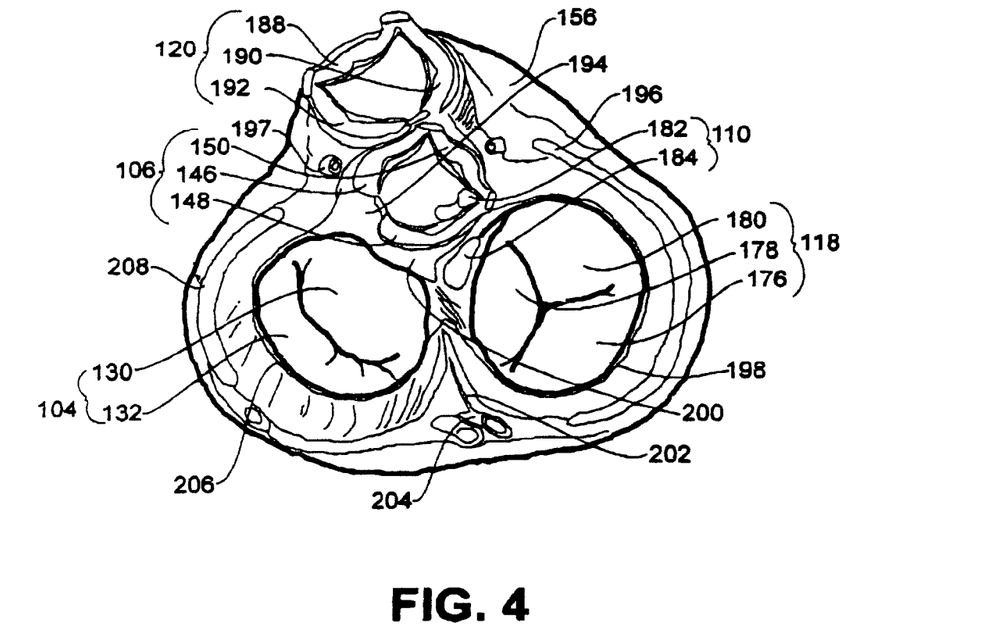
FIG. 4 schematically illustrates a horizontal cross-section of the heart in systole showing valve operation.

Referring to FIG. 4 is the heart in systole viewed from the base with the atria removed. All of the parts are essentially the same as in FIG. 3, however, in this figure, aortic valve 106 and pulmonary valve 120 are shown open and tricuspid valve 118 and mitral valve 104 are shown closed. Again, pulmonary valve 120 has anterior semi-lunar cusp 188, right semi-lunar cusp 190, and left semi-lunar cusp 192. Aortic valve 106 is made up of right (coronary) semi-lunar cusp 150, left (coronary) semi-lunar cusp 146, and posterior (non-coronary) semi-lunar cusp 148. Mitral valve 104 is shown with anterior cusp 130 and posterior cusp 132 surrounded by left fibrous ring 206. Tricuspid valve 118 is shown with anterior cusp 180, septal cusp 178, posterior cusp 176, surrounded by right fibrous ring of tricuspid valve 198. Right coronary artery is shown as 196 with atrial ventricular branch 202 of right coronary artery 196 and posterior interventricular branch 204 of right coronary artery 196 showing. Left coronary artery 197 is also shown. Other parts of the heart shown in B are the same as those shown in A.

The oxygenated blood of the body originates in heart 100 and is pumped by the left ventricle (not shown) into aorta 128. From aorta 128, some blood is supplied to heart 100 through right coronary artery 196 and left coronary artery 197, the remaining blood branches throughout the rest of the body. A first branch, subclavian artery feeds axillary artery which turns into brachial artery to feed blood to the arms. Brachial artery in turn feeds radial artery and ulnar artery. Another branch off of aorta 128 is common carotid artery which feeds blood to the head. Superior mesenteric artery and inferior mesenteric artery feed blood to the abdomen. There is a common iliac artery for both legs. The common iliac artery in turn branches into external iliac artery and femoral artery. One of the branches of femoral artery is popliteal artery which branches into anterior tibial artery, posterior tibial artery, and dorsalis pedis artery. Peroneal artery branches off of external iliac artery.

The deoxygenated blood returns to heart 100 through the venous system. Some blood returning from the legs flows into posterior tibial vein, and anterior tibial vein, which feed into popliteal vein, and flows into femoral vein. Another vein in the legs is great saphenous vein which also feeds into femoral vein. Blood then flows into either internal iliac vein or external iliac vein which then flow into common iliac vein to return to heart 100 via inferior vena cava 284. Other branches feeding into inferior vena cava 284 include hepatic vein. Blood returning from the arms flows into ulnar vein, radial vein, brachial vein, or basilic vein, and flows into axillary vein. Blood flows from axillary vein into left or right innominate vein which flows into superior vena cava. Blood also flows into superior vena cava 278 from right subclavian vein, and from external jugular vein and internal jugular vein.

Figure 5:
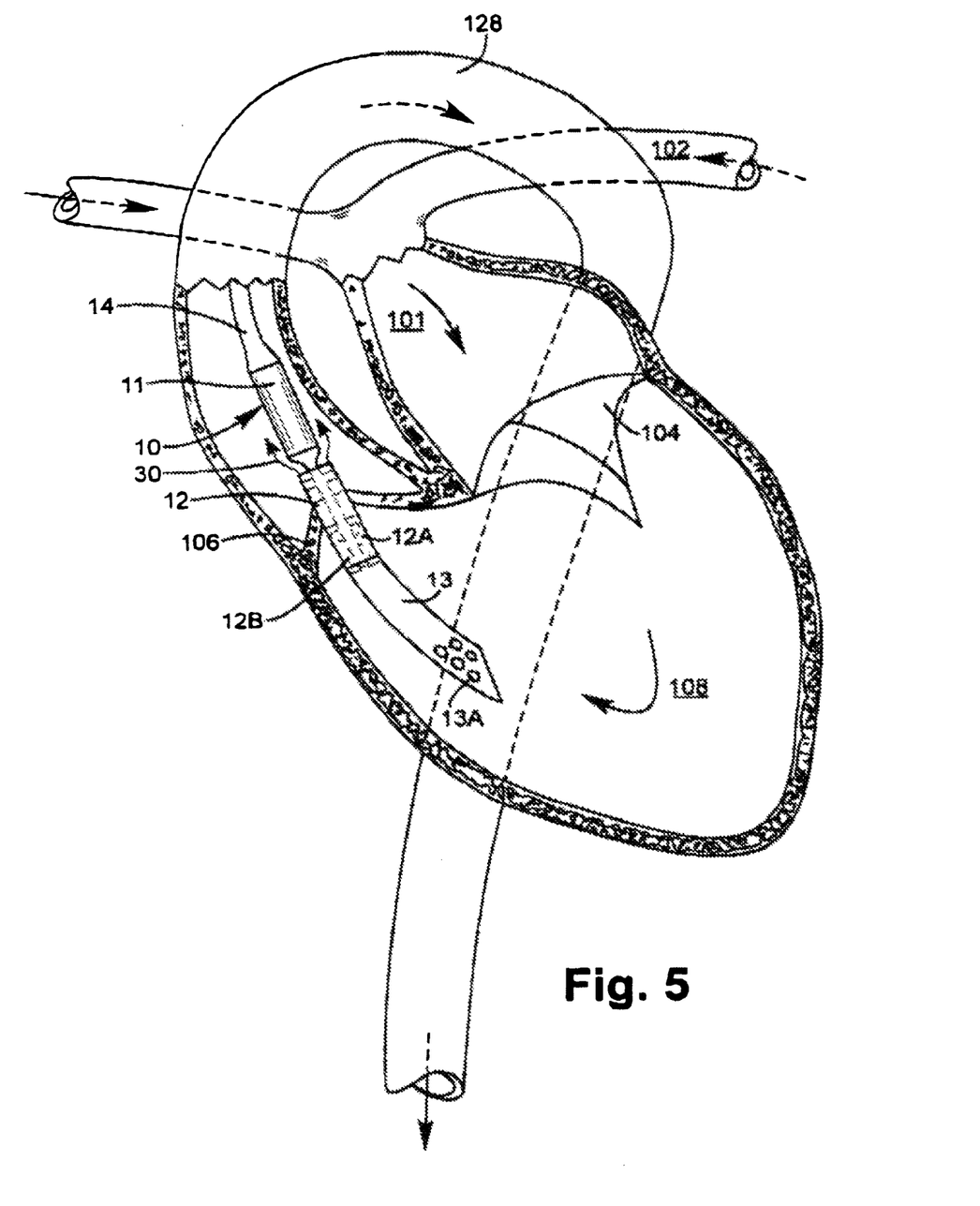
FIG. 5 schematically illustrates a pumping device across the aortic valve.

Referring now to FIG. 5, which schematically illustrates pumping device 10 across aortic valve 106. In one embodiment, suitable blood pumping device 10 is disclosed in U.S. Pat. No. 6,276,848, issued on Jan. 23, 2001, and assigned to Impella Cardiotechnik GmbH. U.S. Pat. No. 6,276,848 is herein incorporated by reference in its entirety. In another embodiment, a suitable blood pumping device 10 is disclosed in U.S. Pat. No. 6,136,025, issued on Oct. 24, 2000. U.S. Pat. No. 6,136,025 is herein incorporated by reference in its entirety. In another embodiment, a suitable blood pumping device 10 is disclosed in U.S. Pat. No. 5,947,892, issued on Sep. 7, 1999, and assigned to MicroMed Technology, Inc. U.S. Pat. No. 5,947,892 is herein incorporated by reference in its entirety. In another embodiment, a suitable blood pumping device is any blood pumping device that is sized to fit within a blood vessel and allow a sufficiently-sized, annular space around or about blood pumping device 10 in which to perform procedures or to fit another catheter and/or a tool. As previously described, blood flows into pulmonary veins 102 and into left atrium 101, across mitral valve 104, and into left ventricle 108. From left ventricle 108, the blood passes through aortic valve 106 and into aorta 128. In this embodiment, there is illustrated pumping device 10 which includes motor unit 11 and pump unit 12 arranged coaxially in series. Pump unit 12 is extended on its distal end by suction hose 13 which has openings 13A for blood supply to the pump. In the representation shown, suction device or hose 13 is located in left ventricle 108. The proximal end of pump unit 12 is connected to the distal end of motor unit 11. The proximal end of motor unit 11 is connected to catheter 14 which has been introduced into aorta 128. One representative way pumping device 10 and catheter 14 may be introduced as illustrated is by feeding the device and catheter through a femoral artery (perhaps through a guide catheter previously positioned into aorta 128, or over a guide wire previously positioned into aorta 128).

Blood flows into suction hose 13 through pump unit 12 and exits as shown by the arrows marked 30 near the distal end of motor unit 11 and adjacent to the proximal end of pump unit 12. In one embodiment, inlet of pump unit 12 is on the distal side of aortic valve 106, and the pump outlet of pump unit 12 is on the proximal side of aortic valve 106. In one embodiment, aortic valve 106 will, in the closed position, abut the outer side of pump unit 12 or suction hose 13.

In one embodiment, catheter 14 is fed through common carotid artery and into aorta 128. In another embodiment, catheter 14 is fed into subclavian artery through brachial artery. In another embodiment, catheter 14 is fed into femoral artery through common iliac artery and into aorta 128. In another embodiment, catheter 14 is fed directly into either one of common iliac artery or lower branch of aorta.

Figure 6:
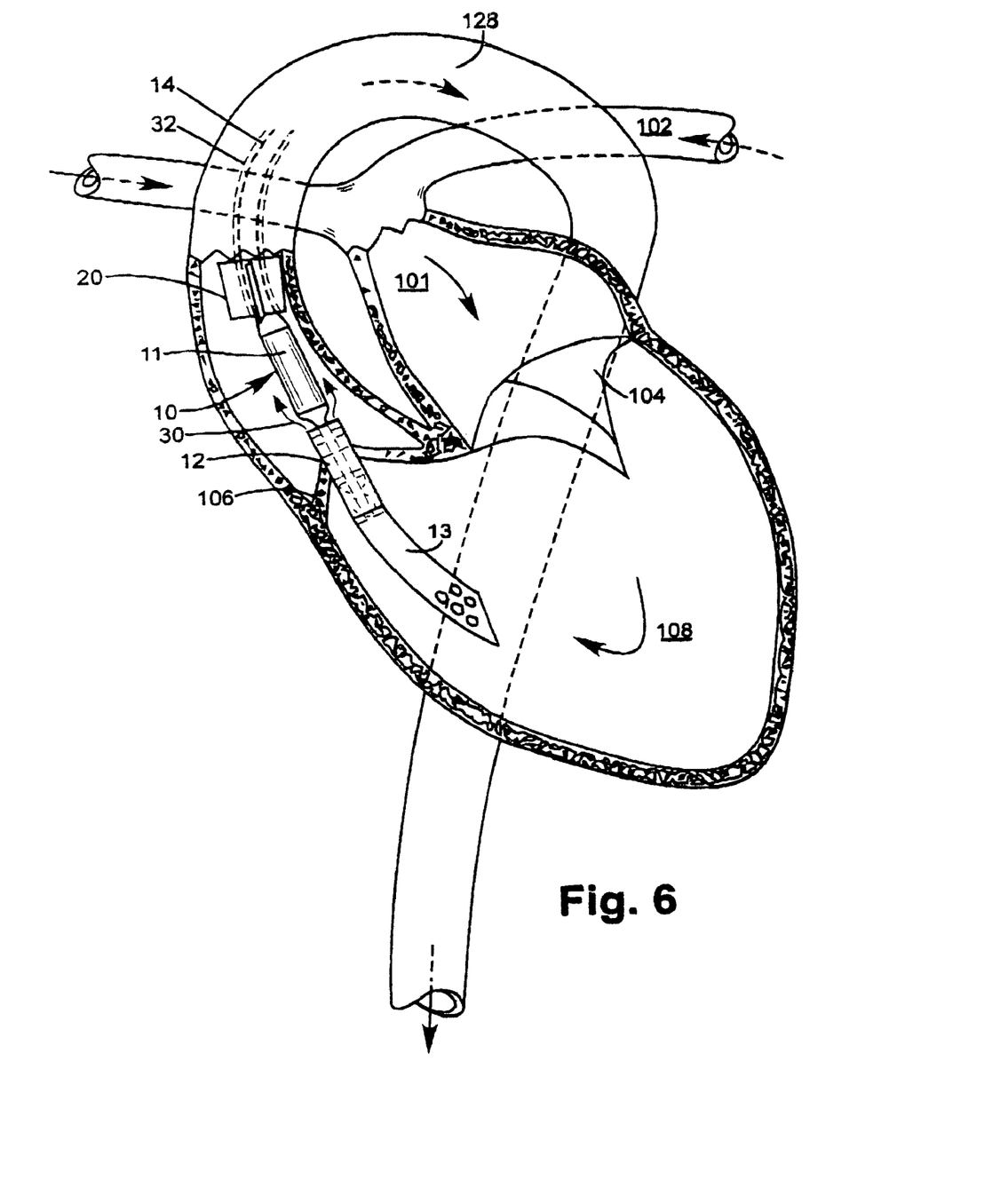
FIG. 6 schematically illustrates a tool being advanced over the pump.

Referring now to FIG. 6, which schematically illustrates tool 20 being advanced over pumping device 10 (including motor unit 11 and pump unit 12). At the distal end of pump unit 12 is suction device 13. The pump inlet on suction device 13 is distal to aortic valve 106, and the pump outlet (adjacent to the proximal end of pump unit 12 and adjacent to the distal end of motor unit 11) marked by arrows 30 is proximal to aortic valve 106. Pumping device 10 is at the distal end of catheter 14. In this embodiment, catheter 14 is used as a guide for second catheter 32 which has at its distal end tool 20. In this embodiment, tool 20 is an arthectomy device being advanced over first catheter 14 through aorta 128.

Figure 7:
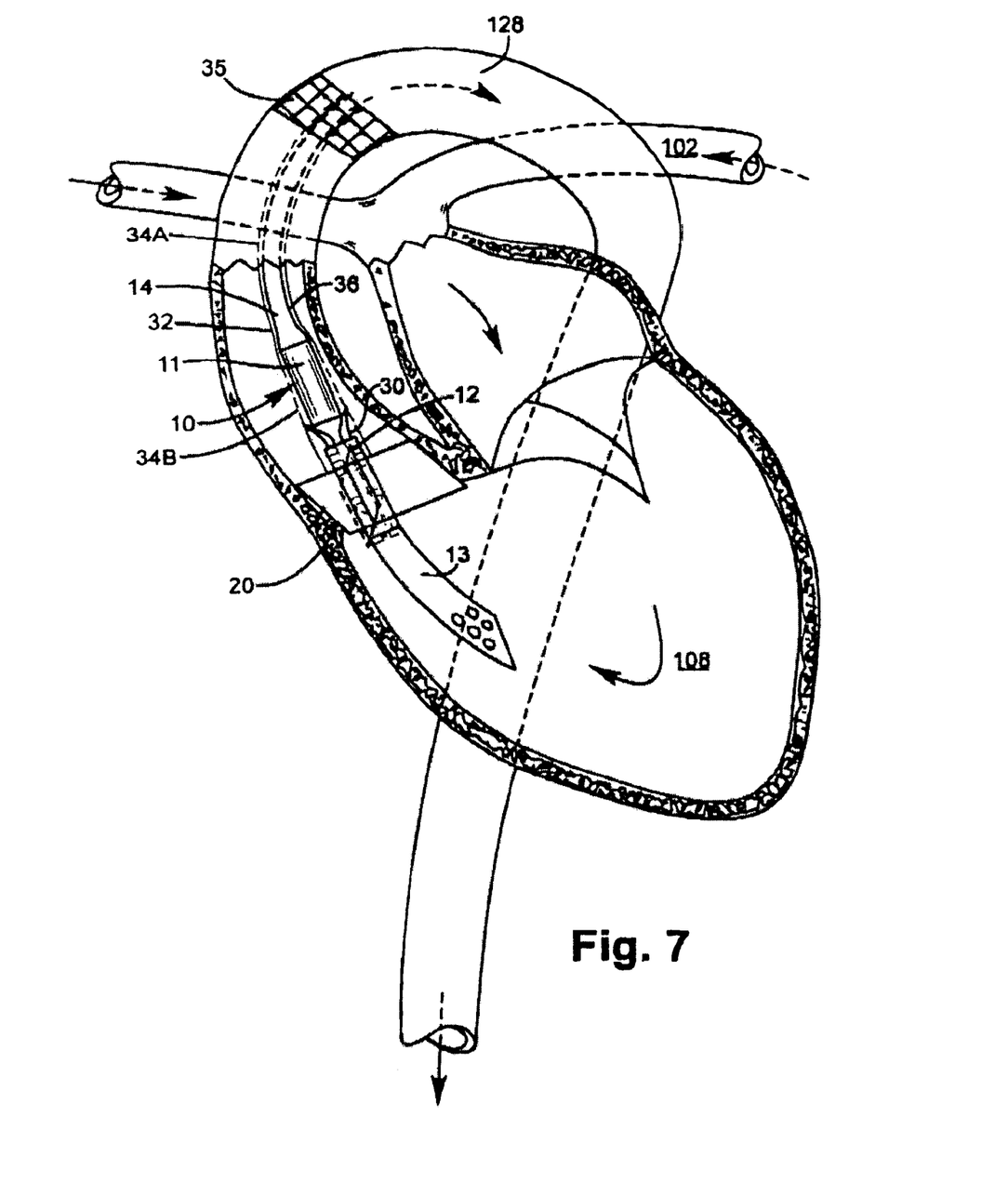
FIG. 7 schematically illustrates a tool removing the aortic valve.

Referring now to FIG. 7, there is schematically illustrated tool 20 which is in place and being used. In one embodiment, tool 20 is an arthectomy device, which may be used to remove valves or other tissue. In this embodiment, arthectomy device 20 has removed the aortic valve. Arthectomy device 20 may include one or more blades which, in this embodiment, can be spun by rotating catheter 34. The inlet of pump 10 is suction device 13. The pump outlet is at the proximal end of pump unit 12 and is marked by arrows 30. The blood flowing out of the pump outlet flows through annular space 36 between inner catheter 14 and outer catheter 32.

In the embodiment shown in FIG. 7, filter 35 is attached to catheter 34 to capture surgical debris. U.S. Pat. No. 5,947,995 discloses a suitable filter that could be placed downstream of tool 20 and/or 22 and downstream of pumping device 10 to remove debris in the blood vessel. U.S. Pat. No. 5,947,995 is herein incorporated by reference in its entirety. In one embodiment, filter 35 is placed distal to coronary arteries 196, 197 (see FIGS. 3 and 4) to remove debris before it enters coronary arteries 196, 197.

Eventually, blood exits annular space 36 by holes or perforations 34A in outer catheter 32. In another embodiment, there may be provided holes or perforations 34B adjacent to the openings of coronary arteries 196, 197 (see FIGS. 3 and 4). In one embodiment, the pump inlet is distal to tool 20, and the pump outlet is proximal to tool 20. Accordingly, so a procedure can be carried out using the tool (e.g., removal and replacement of aortic valve) using pumping device 10 as a substitute for the pumping action of left ventricle 108 and aortic valve 106. Thus, a procedure may be carried out without cardiopulmonary bypass.

Figure 8:
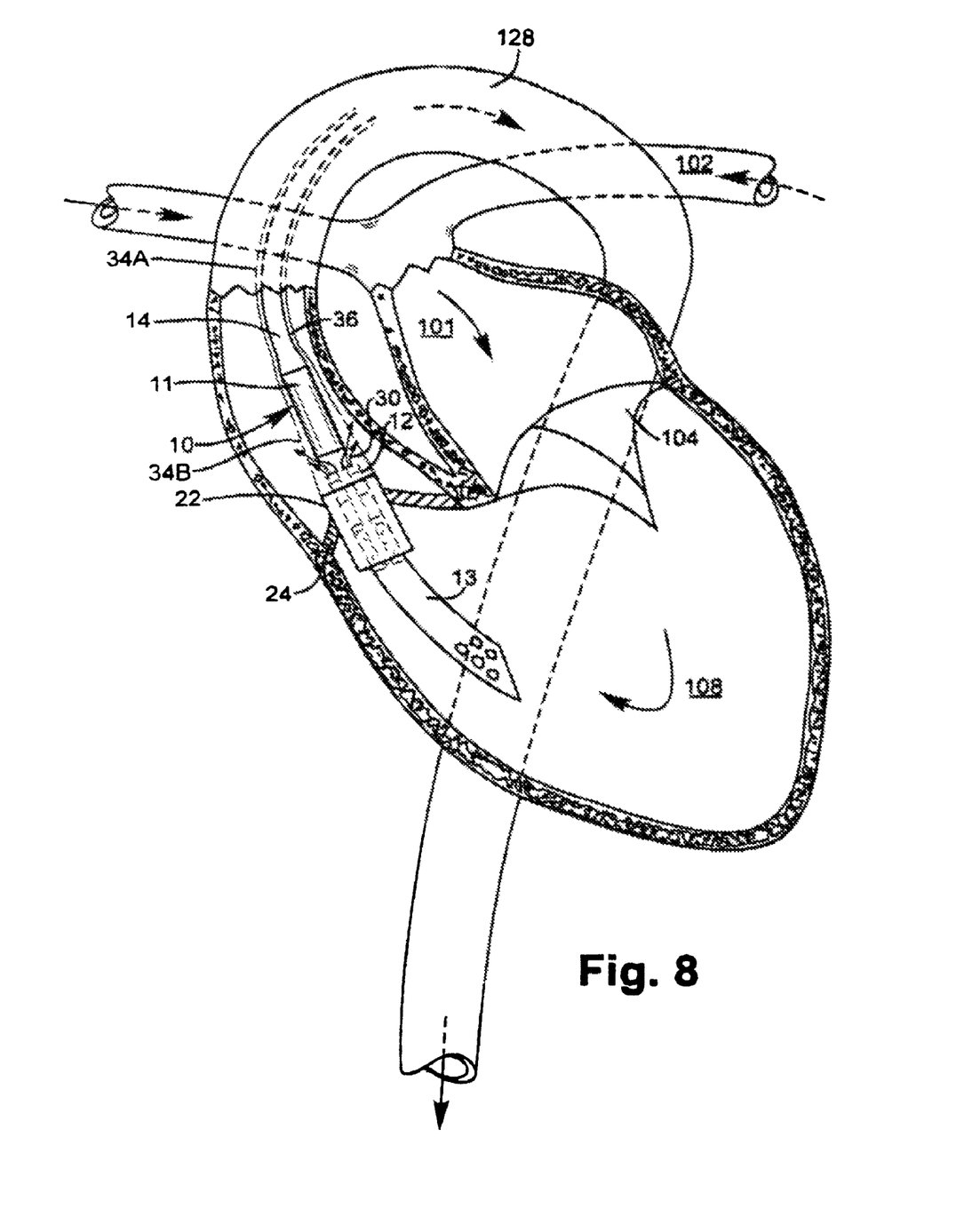
FIG. 8 schematically illustrates a tool implanting a replacement aortic valve.

Referring now to FIG. 8, there is illustrated tool 22 which is installing prosthetic valve 24. Pumping device 10 is in aorta 128 at the distal end of catheter 14. Pumping device 10 is made up of pump unit 12 and motor unit 11. At the distal end of pump unit 12 is a pump inlet, which is shown in this embodiment as suction device 13. At the proximal end of pump unit 12 is the pump outlet marked by arrows 30. Exterior to catheter 14 is second catheter 32, with annular space 36 between interior catheter 14 and exterior catheter 32. The blood flows into the pump inlet, in this embodiment, suction device 13, through pump 12 and to pump outlet 30, through annular space 36, and out of the holes or perforations 34A of exterior catheter 32 and into aorta 128. In another embodiment, there may be provided holes or perforations 34B adjacent to the openings of coronary arteries 196, 197 (see FIGS. 3 and 4). There is tool 22 at the distal end of catheter 32. In this embodiment, tool 22 is being used to implant prosthetic aortic valve 24. U.S. Pat. No. 6,168,614 discloses a suitable tool 20 and/or 22 and replacement valve prosthesis 24. U.S. Pat. No. 6,168,614 is herein incorporated by reference in its entirety.

Figure 9:
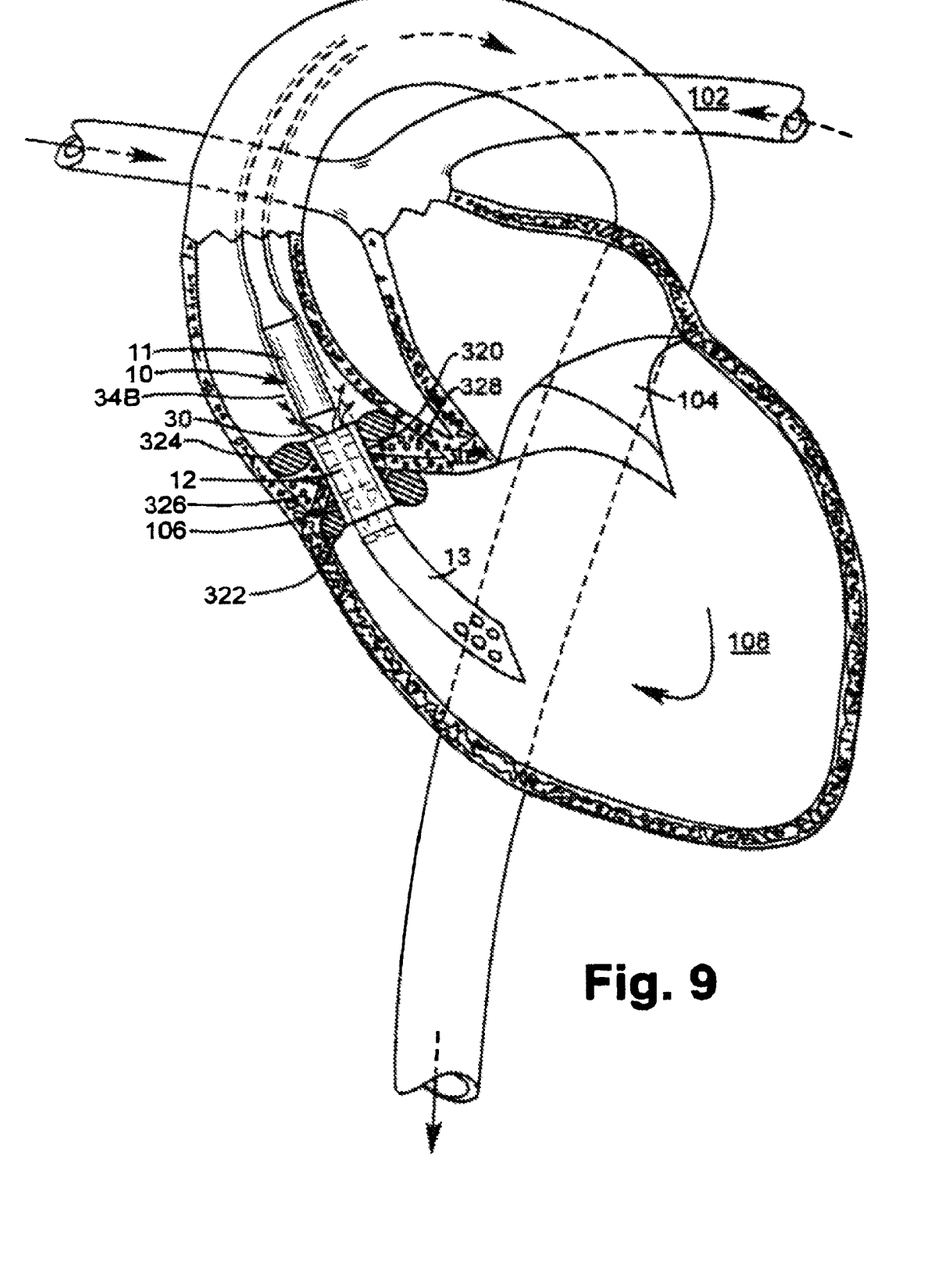

Referring now to FIG. 9, there is illustrated tool 320, which has been advanced over pumping device 10 (including motor unit 11 and pump unit 12). At the distal end of pump unit 12 is suction device 13. The pump inlet on suction device 13 is distal to aortic valve 106, and the pump outlet (adjacent to the proximal end of pump unit 12 and adjacent to the distal end of motor unit 11) marked by the arrows 30 is proximal to aortic valve 106. Pumping device 10 is at the distal end of first catheter 14. In this embodiment, first catheter 14 is used as a guide for second catheter 32, which has at its distal end tool 320. In this embodiment, tool 320 includes first sealing mechanism 322 distal to aortic valve 106 and a second sealing mechanism 324 proximal to aortic valve 106. Liquid treatment 326 may be provided in isolated area 328 between first sealing mechanism 322 and second sealing mechanism 324 to treat aortic valve 106. In one embodiment, first sealing mechanism 322 is a balloon catheter. In another embodiment, second sealing mechanism 324 is a balloon catheter. In one embodiment, liquid treatment 326 is a therapeutic fluid. One example of a suitable therapeutic fluid is Corazon Demineralization Solution (CDS) available from the Corazon Technologies Corporation. CDS or other therapeutic fluids may be used to remove calcium or other deposits from aortic valve 106. A lumen (not shown) may be provided in first catheter 14 or second catheter 32 to provide treatment agent 326 and to evacuate treatment agent 326 from isolated area 328 between first sealing mechanism 322 and second sealing mechanism 324.

In one method of use, first catheter is advanced so that suction device 13 is located in left ventricle 108, and pumping device 10, including motor unit 11 and pump unit 12, is located across aortic valve 106. Next, second catheter 32 may be advanced over first catheter 14 to locate tool 320 across aortic valve 106. Once tool 320 is across aortic valve 106, first sealing mechanism 322 and second sealing mechanism 324 may be activated, while pumping device 10 is activated to establish a flow of blood into suction device 13 through pump unit 12 and to pump outlet marked by arrows 30. Blood may flow out of pump outlet marked by arrows 30 through perforations 34B and/or through perforations 34A. Perforations 34B are provided adjacent to the openings of coronary arteries 196, 197 (see FIGS. 3 and 4). Once the pumping device 10 has been activated and the flow of blood begins through pumping device 10, blood may be evacuated from the area to be isolated between first sealing mechanism 322 and second sealing mechanism 324. Once blood has been evacuated from isolated area 328, treatment agent 326 may be introduced into isolated area 328. After a sufficient amount of time for the treatment agent 326 to be effective, treatment agent 326 may be evacuated from isolated area 328, first sealing mechanism 322 and second sealing mechanism 324 may be deactivated, and first catheter 14 and second catheter 42 can be removed from the patient's body and the normal flow of blood can resume in heart 100.

In another embodiment, using pumping device 10 in conjunction with a treatment agent 326 may enhance safety and permit added time to conduct a fluid therapy.

In another embodiment, pump 10 and tool 20 and/or tool 22 can be used for mitral valve repair 104 by feeding catheter 14 and catheter 32 through left ventricle 108 to mitral valve 104. In this embodiment, the pump inlet, such as suction device 13, is located in left atrium 101, distal to mitral valve 104. The pump outlet (marked by arrows 30 in FIGS. 5-9) is proximal to mitral valve 104, so that a mitral valve repair or replacement can be carried out while still allowing blood flow from left atrium 101 to left ventricle 108. The blood can flow out of the pump outlet marked by arrows 30 into annular space 36 between inner catheter 14 and outer catheter 32 and exit at holes or perforations 34. In one embodiment, holes or perforations 34 can be located in left ventricle 108, and in another embodiment in aorta 128. U.S. Pat. No. 6,312,447 discloses a suitable tool 20 and/or 22 to repair or replace mitral valve 104. U.S. Pat. No. 6,312,447 is herein incorporated by reference in its entirety.

In another embodiment, first catheter 14 and/or second catheter 32 can be fed through the venous system and into any of the veins of the venous system and into inferior vena cava 116 or superior vena cava 126 and into right artium 122 in order to repair or replace, for example, tricuspid valve 118 (see FIG. 1). Those skilled in the art will appreciate that the pump inlet shown as 13 and the pump outlet marked by arrows 30 will be reversed when used on the right side of the heart since blood flows into the right side of the heart and out of the left side of the heart, so the pumping will be done in the opposite direction in accordance with the natural blood flow of the heart.

In another embodiment, first catheter 14 and/or second catheter 32 can be fed into right atrium 122 across tricuspid valve 118 and be used for a septal defect repair of septum 110.

In another embodiment, first catheter 14 and/or second catheter 32 can be fed into right atrium 122 across tricuspid valve 118 and into right ventricle 114 and be used for repair or replacement of the pulmonary valve 120.

In another embodiment, first catheter 14 and/or second catheter 32 can be fed through aorta 128 across aortic valve 106 into left ventricle 108 and used to repair a septal defect of septum 110.

In another embodiment, pumping device 10 is used so that the pump inlet, in this embodiment suction device 13, is distal to the area being worked on, while the pump outlet, marked by arrows 30, is proximal to the area being worked on, so that blood can be routed through pumping device 10 while a procedure is being conducted. This allows a procedure to be conducted while blood flow continues without the use of cardiopulmonary bypass.

In one embodiment, there is a device adapted to be used for percutaneous minimally invasive heart surgery that includes catheter 14 that has a proximal end and a distal end adapted to be fed through a blood vessel, pump 10 attached to the distal end of catheter 14, and tool 20 and/or 22 attached to the distal end of catheter 14 adapted to be used for percutaneous minimally invasive heart surgery.

In one embodiment, catheter 14 has pump 10 attached to distal end of catheter 14. Pump inlet 13 is provided at distal end of pump 10. Tool 20 and/or 22 is provided proximal to pump inlet 13. Pump outlet 30 is provided proximal to tool 20 and/or 22, and proximal to pump inlet 13.

In another embodiment, pump outlet 30 is provided at distal end of catheter 14. Tool 20 and/or 22 is provided proximal to pump outlet 30. Pump inlet 13 is provided proximal to tool 20 and/or 22, and proximal to pump outlet 30.

In another embodiment, pump 10 also includes lumen 12A therethrough.

In another embodiment, tool 20 and/or 22 may be one or more of a tool for excising natural tissue, a tool for excising a natural valve, an athrectomy device, a prosthetic valve delivery system, a balloon catheter, a stent delivery catheter, a knife, a stapler, a screwdriver, a suturing system with sutures, or combinations thereof, for example, including a prosthetic valve and a device to place the valve.

In another embodiment, the device also includes filter 35 attached to catheter 14 proximal to tool 20 and/or 22 and proximal to pump 10, where the filter 35 is adapted to capture surgical or other types of debris in the blood vessel.

In another embodiment, pump 10 also includes at least one impeller blade 12B.

In another embodiment, a percutaneous minimally invasive heart surgery suitable for a device such as described may include one or more of aortic valve repair, aortic valve replacement, mitral valve repair, mitral valve replacement, tricuspid valve repair, tricuspid valve replacement, pulmonary valve repair, pulmonary valve replacement, bowtie valve repair (Alfieri's), atrial septal defect repair, coronary artery revascularization such as angioscopic laser introduction or angioscopic balloon, angioplasty catheter, or sinus zenosus defect repair, infundibular stenosus relief by cardioscopic techniques, pulmonary valvular stenosus relief by cardioscopic techniques, aortic stenosus relief by the introduction of instrumentation by a lumen in the aortic catheter into the aortic route, chordae tendineae repair or replacement, papillary muscle repair, replacement, or realignment.

In another embodiment, there is disclosed a kit adapted to be used for percutaneous minimally invasive heart surgery that includes, with reference to FIGS. 5-9, first catheter 14 adapted to be fed through a blood vessel, where first catheter 14 includes a proximal end and a distal end, pump 10 at the distal end of first catheter 14, second catheter 32 adapted to be fed through a blood vessel, where second catheter 32 comprises a proximal end and a distal end, and tool 20 and/or 22 on the distal end of second catheter 32. In one embodiment, first catheter 14 and second catheter 32 have a coaxial relationship such that second catheter 32 is fed over first catheter 14. In another embodiment, first catheter 14 and second catheter 32 are fed through the same vessel of the patient so that the distal ends of the catheters are adjacent to each other. In another embodiment, first catheter 14 and second catheter 32 are fed through different vessels of the patient so that the distal ends of the catheters are in close proximity to each other.

In another embodiment, there is disclosed a method of performing a percutaneous minimally invasive heart surgery that includes feeding catheter 14 having pump 10 at a distal end of catheter 14 into a patient's blood vessel, placing inlet 13 of pump 10 into patient's left ventricle 108, and placing outlet 30 of pump 10 in patient's aorta 128.

In another embodiment, the method also includes feeding tool 20 and/or 22 at the distal end of catheter 14 into either patient's aorta 128, left ventricle 108, and left atrium 101.

In another embodiment, the method also includes feeding tool 20 and/or 22 at a distal end of second catheter 32 into a patient's blood vessel.

In another embodiment, the blood vessel may include one or more of aorta 128, pulmonary artery 124, superior vena cava 126, inferior vena cava 116, and pulmonary vein 102.

Other uses of percutaneous heart repairs and other types of surgeries are contemplated for use with this invention which may be used to affect percutaneous surgeries without the use of cardiopulmonary bypass.

In one embodiment, the pumping device and tool 20 and/or tool 22 may be located on the same catheter 14. In another embodiment, pumping device 10 may be on the distal end of catheter 14, and tool 20 and/or 22 may be on the distal end of second catheter 32. In one embodiment, first catheter 14 and second catheter 32 have a coaxial relationship. In another embodiment, first catheter 14 and second catheter 32 are located side by side within a blood vessel. In another embodiment, first catheter 14 is fed through a first blood vessel, and second catheter 32 is fed through a second blood vessel so that tool 20 and/or 22 and pumping device 10 are in close proximity to one another. In another embodiment, first catheter 14 and second catheter 32 are located side by side both within a lumen of a third catheter (not shown).

In the preceding detailed description, the invention is described with reference to specific embodiments thereof. It will, however, be evident that various modifications and changes may be made thereto without departing from the broader spirit and scope of the invention as set forth in the claims. The specification and drawings are, accordingly, to be regarded in an illustrative rather than a restrictive sense.

The invention claim is:

1. A method comprising:
feeding a first catheter having a pump associated with a distal end of the catheter into a patient's blood vessel;
placing an inlet of the pump into a left ventricle of the patient;
placing an outlet of the pump in an aorta of the patient;
after placing the pump, using the first catheter as a guide, feeding a second catheter comprising a tool over the first catheter to at least one of the aorta of the patient, the left ventricle of the patient, and a left atrium of the patient; and
performing a percutaneous procedure with the tool on the patient,
wherein the pump is used to maintain blood flow around or through an area of the procedure.

2. The method of claim 1, wherein the tool is a first tool, the method further comprising:
after feeding the first tool, feeding a second tool into a patient's blood vessel.

3. The method of claim 1, wherein the tool is a first tool, the method further comprising:
feeding a second tool at a distal end of the second catheter into a patient's blood vessel.

4. The method of claim 2, wherein the blood vessel is selected from the group consisting of the aorta, the pulmonary artery, the superior vena cava, the inferior vena cava, and the pulmonary vein.

5. The method of claim 2, wherein the first tool comprises a tool for excising one of natural tissue and natural valves, and the second tool comprises a tool to implant a prosthesis.

6. The method of claim 3, wherein the first tool comprises a tool for excising one of natural tissue and natural valves, and the second tool comprises a tool to implant a prosthesis.

7. A method comprising:
feeding a first catheter having a pump associated with a distal end of the catheter into a patient's blood vessel;
placing an inlet of the pump into a left ventricle of the patient;
placing an outlet of the pump in an aorta of the patient;
maintaining a blood flow around or through an area identified for a percutaneous procedure; and
using the first catheter as a guide, feeding a second catheter comprising a tool over the first catheter in at least one of the aorta of the patient, the left ventricle of the patient, and a left atrium of the patient.

8. The method of claim 7, further comprising:
performing a percutaneous procedure on the patient.

9. The method of claim 8, wherein the tool is a first tool, the method further comprising:
after feeding the first tool, feeding a second tool into a patient's blood vessel.

10. The method of claim 8, wherein the tool is a first tool, the method further comprising:
feeding a second tool at a distal end of the second catheter into a patient's blood vessel.

11. The method of claim 9, wherein the blood vessel is selected from the group consisting of the aorta, the pulmonary artery, the superior vena cava, the inferior vena cava, and the pulmonary vein.

12. The method of claim 9, wherein the first tool comprises a tool for excising one of natural tissue and natural valves, and the second tool comprises a tool to implant a prosthesis.

13. The method of claim 10, wherein the first tool comprises a tool for excising one of natural tissue and natural valves, and the second tool comprises a tool to implant a prosthesis.

* * * * *